US010280467B2

(12) United States Patent
Saijo et al.

(10) Patent No.: US 10,280,467 B2
(45) Date of Patent: May 7, 2019

(54) QUANTIFICATION METHOD FOR EXPRESSION LEVEL OF WT1 MRNA

(71) Applicant: OTSUKA PHARMACEUTICAL CO., LTD., Tokyo (JP)

(72) Inventors: Yoko Saijo, Osaka (JP); Ryuta Ito, Osaka (JP); Daisuke Koga, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 367 days.

(21) Appl. No.: 14/762,454

(22) PCT Filed: Jan. 22, 2014

(86) PCT No.: PCT/JP2014/051294
§ 371 (c)(1),
(2) Date: Jul. 21, 2015

(87) PCT Pub. No.: WO2014/115779
PCT Pub. Date: Jul. 31, 2014

(65) Prior Publication Data
US 2016/0333415 A1 Nov. 17, 2016

(30) Foreign Application Priority Data
Jan. 22, 2013 (JP) ................. 2013-008984

(51) Int. Cl.
C12P 19/34 (2006.01)
C12Q 1/6886 (2018.01)
C12Q 1/6851 (2018.01)

(52) U.S. Cl.
CPC ......... *C12Q 1/6886* (2013.01); *C12Q 1/6851* (2013.01); *C12Q 2600/158* (2013.01); *C12Q 2600/16* (2013.01)

(58) Field of Classification Search
USPC .............................. 435/6.12, 91.2
See application file for complete search history.

(56) References Cited

U.S. PATENT DOCUMENTS

| 2007/0031966 A1 | 2/2007 | Dressler et al. |
| 2007/0264635 A1 | 11/2007 | Suzuki et al. |
| 2010/0304390 A1 | 12/2010 | Sanders et al. |

FOREIGN PATENT DOCUMENTS

| CN | 101182570 A | 5/2008 |
| CN | 101760522 A | 6/2010 |
| CN | 101781677 A | 7/2010 |
| CN | 102443581 A | 5/2012 |
| CN | 102459648 A | 5/2012 |
| CN | 102534045 A | 7/2012 |
| JP | 11-89596 | 4/1999 |
| JP | 11-89599 | 4/1999 |
| JP | 2002-136300 | 5/2002 |
| JP | 2006-223303 | 8/2006 |
| JP | 2009-509502 | 3/2009 |
| JP | 2012-525825 | 10/2012 |
| WO | WO 2007/035676 A2 | 3/2007 |
| WO | WO 2010/128024 A2 | 11/2010 |

OTHER PUBLICATIONS

Critical Factors for Successful Real-Time PCR Brochure, Qiagen, Jul. 20, 2010.
The Japanese Journal of Clinical Hematology, 2005, vol. 46, No. 12, pp. 1279-1287.
Shimada, Akira et al., "High WT1 mRNA expression after induction chemotherapy and FLT2-ITD have prognostic impact in pediatric acute myeloid leukemia: a study of the Japanese Childhood AML Cooperative Study Group,"International Journal of Hematology, 2012, vol. 96, No. 4, pp. 469-476.
Office Action for corresponding Japanese Patent Application No. 2014-558599 dated April 11, 2017.
Critical Factors for Successful Real-Time PCT Brochure, Qiagen, Jul. 20, 2010.
Office Action for corresponding Korean Patent Application No. 10-2015-7022395 dated Mar. 20, 2017.
Anuchapreeda, Songyot, "Effect of Pure Curcumin, Demethoxycurcumin, and Bisdemethoxycurcurmin on WT1 Gene Expression in Leukemic Cell Lines," Cancer Chemotherapy and Pharmacology, Nov. 23, 2007, vol. 62, No. 4, pp. 585-594.
Pei, Ying et al., "Aldehyde Dehydrogenase (ALDH) 3A1 Expression by the Human Keratocyte and its Repair Phenotypes," Experimental Eye Research, Nov. 1, 2006, vol. 83, No. 5, pp. 1063-1073.
Sanz, Eva et al., "Human Cord Blood CD34+Pax-5+ B-cell Progenitors: Single-Cell Analyses of their Gene Expression Profiles," Blood, The American Society of Hematology, May 1, 2003, vol. 101, No. 9, pp. 3424-3430.
Satelli, Arun et al., "Galectin-1 is Silenced by Promoter Hypermethylation and its Re-Expression Induces Apoptosis in Human Colorectal Cancer Cells," Cancer Letters, Feb. 1, 2011, vol. 301, No. 1, pp. 38-46.
Siehl, JM, et al., "Tumour Cell Contamination, Quantitative Real-Time RT-PCR Detects Elevated Wilms Tumor Gene (WT1) Expression in Autologous Blood Stem Cell Preparations (PBSCs) From Actue Myeloid Leukemia (AML) Patients Including Contamination with Leukemic Blasts,"Bone Marrow Transplantation, Mar. 1, 2002, pp. 379.

(Continued)

Primary Examiner — Kenneth R Horlick
(74) Attorney, Agent, or Firm — Finnegan, Henderson, Farabow, Garrett & Dunner, LLP

(57) ABSTRACT

A method for quantifying the expression level of human WT1 mRNA conveniently, in a short period of time, and with high sensitivity is provided. The method can be used for diagnosing cancer, such as leukemia and solid cancer, or for determining when to perform bone marrow transplantation. The method is for quantifying the expression level of human WT1 mRNA by one-step RT-PCR and comprises simultaneously subjecting the human WT1 mRNA and a housekeeping gene (mRNA) to reverse transcription and extension reactions carried out sequentially in the same vessel.

4 Claims, 5 Drawing Sheets
Specification includes a Sequence Listing.

(56) References Cited

OTHER PUBLICATIONS

Supplementary European Search Report for corresponding EP Application No. 14743826.1 dated Jul. 27, 2016.
Sasaki, "Experimental Medicine Bessatsu Mokutekibetsu de Eraberu PCR Jikken Purotokoru [PCR Experimental Protocols That Can Be Selected According to the Purpose]", pp. 45, 46, and 201, (2011).
P. Nirdé et al., "Quantitation of Androgen Receptor Messenger RNA from Genital Skin Fibroblasts by Revere Transcription—Competitive Polmerase Chain Reaction", The Journal of Steroid Biochemistry and Molecular Biology, vol. 66, No. 1-2, pp. 35-43, (1998).
K. Call et al., "Isolation and Characterization of a Zinc Finger Polypeptide Gene at the Human Chromosome 11 Wilms' Tumor Locus", Cell, vol. 60. No. 3, pp. 509-520, (1990).
Y. Oji et al., "Expression of the Wilms' Tumor Gene WT1 In Solid Tumors and Its Involvement in Tumor Cell Growth", Japanese Journal of Cancer Research, vol. 90, No. 2, pp. 194-204, (1999).
H. Miwa et al., "Expression of the Wilms' Tumor Gene (WT1) in Human Leukamias", Leukemia, vol. 6, No. 5, pp. 405-109, (1992).
K. Inoue et al., "WT1 as a New Prognostic Factor and a New Marker for the Detection of Minimal Residual Disease in Acute Leukemia", Blood, vol. 84, No. 9, pp. 3071-3079, (1994).
L. Bergmann et al., "High Levels of Wilms' Tumor Gene (wt1) mRNA in Acute Myeloid Leukemias Are Associated With a Worse Long-Term Outcome", Blood, vol. 90, No. 3, pp. 1217-1225, (1997).
K. Inoue et al., "Long-Term Follow-Up of Minimal Residual Disease in Leukemia Patients by Monitoring WT1 (Wilms Tumor Gene) Expression Levels", Blood, vol. 88, No. 6, pp. 2267-2278, (1996)
H. Tamaki et al., Increased expression of the Wilms tumor gene (WT1) at relapse in acture leukemia [letter], Blood, vol. 88, No. 11, pp. 4396-4398, (1996).
International Search Report from the Japanese Patent Office of PCT International Application No. PCT/2014/051294 dated Apr. 15, 2014.
Carraro, Gianni et al., "Similar Sequence-Free Amplification of Human Glyceraldehyde-3-Phosphate Dehydrogenase for Real Time RT-PCR Applications," Molecular and Cellular Probes, vol. 19, No. 3 (2005) 181-186.
Office Action for corresponding EP Application No. 14743826.1 dated Feb. 27, 2018.
Check using ReverTra AceR gPCR RT Master Mix with gDNA Remover/of example of cDNA specific detection-contamination genome DNA removal performance, 2012, vol. 99, pp. 1-2.
Gil; Joan et al "Impairment of the Proapoptotic Activity of Bax by Missense Mutations Found in Gastrointestinal Cancers," Cancer Research, May 1, 1999, vol. 59, pp. 2034-2037.
Kim, Eun-Joo et al., "IFI16 Is an Essential Mediator of Growth Inhibition, but Not Differentiation, Induced by the Leukemia Inhibitory Factor/JAK/STAT Pathway in Medullary Thyroid Carcinoma Cells," The Journal of Biological Chemistry, 2005, vol. 280, No. 6. pp. 4913-4920.
Ogi, Kazuhiro et al., "Aberrant Methylation of Multiple Genes and Clinicopathological Features in Oral Squamous Cell Carcinoma," Clinical Cancer Research, 2002, vol. 8, pp. 3164-3171.
Real-Time RT-PCR Laboratory Procedure, 2008, pp. 1-11.
Office Action for corresponding Japanese Patent Application No. 2014-558599 dated Nov. 21, 2017.

```
SEQUENCE LISTING

<160> NUMBER OF SEQ ID NOS: 13

<210> SEQ ID NO 1
<211> LENGTH: 3037
<212> TYPE: DNA
<213> ORGANISM: Homo sapiens

<400> SEQUENCE: 1
agctggggta aggagttcaa ggcagcgccc acacccgggg gctctccgca acccgaccgc        60
ctgtccgctc ccccacttcc cgccctccct cccacctact cattcaccca cccacccacc       120
cagagccggg acgcagccc  aggcgccgg  gccccgccgt  ctcctcgccg  cgatcctgga       180
cttcctcttg ctgcaggacc cggcttccac gtgtgtcccg gagccggcgt ctcagcacac       240
gctccgctcc gggcctgggt gcctacagca gccagagcag cagggagtcc gggacccggg       300
cggcatctgg gccaagttag gcgccgccga ggccagcgct gaacgtctcc agggccggag       360
gagccgcggg gcgtccgggt ctgagccgca gcaaatgggc tccgacgtgc gggacctgaa       420
cgcgctgctg cccgccgtcc cctccctggg tggcggcggc ggctgtgccc tgcctgtgag       480
```

```
cggcgcggcg cagtgggcgc cggtgctgga ctttgcgccc ccgggcgctt cggcttacgg    540
gtcgttgggc ggccccgcgc cgccaccggc tccgccgcca cccccgccgc cgccgcctca    600
ctccttcatc aaacaggagc cgagctgggg cggcgcggag ccgcacgagg agcagtgcct    660
gagcgccttc actgtccact tttccggcca gttcactggc acagccggag cctgtcgcta    720
cgggcccttc ggtcctcctc cgcccagcca ggcgtcatcc ggccaggcca ggatgtttcc    780
taacgcgccc tacctgccca gctgcctcga gagccagccc gctattcgca atcagggtta    840
cagcacggtc accttcgacg ggacgcccag ctacggtcac acgccctcgc accatgcggc    900
gcagttcccc aaccactcat tcaagcatga ggatcccatg ggccagcagg gctcgctggg    960
tgagcagcag tactcggtgc cgcccccggt ctatggctgc cacaccccca ccgacagctg   1020
caccggcagc caggctttgc tgctgaggac gccctacagc agtgacaatt tataccaaat   1080
gacatcccag cttgaatgca tgacctggaa tcagatgaac ttaggagcca ccttaaaggg   1140
agttgctgct gggagctcca gctcagtgaa atggacagaa gggcagagca accacagcac   1200
agggtacgag agcgataacc acacaacgcc catcctctgc ggagcccaat acagaataca   1260
cacgcacggt gtcttcagag gcattcagga tgtgcgacgt gtgcctggag tagccccgac   1320
tcttgtacgg tcggcatctg agaccagtga gaaacgcccc ttcatgtgtg cttacccagg   1380
ctgcaataag agatatttta agctgtccca cttacagatg cacagcagga agcacactgg   1440
tgagaaacca taccagtgtg acttcaagga ctgtgaacga aggttttctc gttcagacca   1500
gctcaaaaga caccaaagga gacatacagg tgtgaaacca ttccagtgta aaacttgtca   1560
gcgaaagttc tccggtccg accacctgaa gacccacacc aggactcata caggtaaaac   1620
aagtgaaaag cccttcagct gtcggtggcc aagttgtcag aaaaagtttg cccggtcaga   1680
tgaattagtc cgccatcaca acatgcatca gagaaacatg accaaactcc agctggcgct   1740
ttgaggggtc tccctcgggg accgttcagt gtcccaggca gcacagtgtg tgaactgctt   1800
tcaagtctga ctctccactc ctcctcacta aaaaggaaac ttcagttgat cttcttcatc   1860
caacttccaa gacaagatac cggtgcttct ggaaactacc aggtgtgcct ggaagagttg   1920
gtctctgccc tgcctacttt tagttgactc acaggccctg gagaagcagc taacaatgtc   1980
tggttagtta aaagcccatt gccatttggt gtggattttc tactgtaaga agagccatag   2040
ctgatcatgt cccctgacc cttcccttct tttttttatgc tcgttttcgc tggggatgga   2100
attattgtac cattttctat catggaatat ttataggcca gggcatgtgt atgtgtctgc   2160
taatgtaaac tttgtcatgg tttccattta ctaacagcaa cagcaagaaa taaatcagag   2220
agcaaggcat cgggggtgaa tcttgtctaa cattcccgag gtcagccagg ctgctaacct   2280
ggaaagcagg atgtagttct gccaggcaac ttttaaagct catgcatttc aagcagctga   2340
agaaaaaatc agaactaacc agtacctctg tatagaaatc taaaagaatt ttaccattca   2400
gttaattcaa tgtgaacact ggcacactgc tcttaagaaa ctatgaagat ctgagatttt   2460
tttgtgtatg tttttgactc ttttgagtgg taatcatatg tgtctttata gatgtacata   2520
cctccttgca caaatggagg ggaattcatt ttcatcactg ggagtgtcct tagtgtataa   2580
aaaccatgct ggtatatggc ttcaagttgt aaaaatgaaa gtgactttaa agaaaatag    2640 gggatggtcc aggatctcca ctgataagac tgttttttaag taacttaagg acctttgggt   2700
ctacaagtat atgtgaaaaa aatgagagactt actgggtgag gaaatccatt gtttaaagat   2760
ggtcgtgtgt gtgtgtgtgt gtgtgtgtgt gtgtgtgttg tgttgtgttt tgttttttaa   2820
gggagggaat ttattattta ccgttgcttg aaattactgt gtaaatatat gtctgataat   2880
```

```
gatttgctct tgacaacta aaattaggac tgtataagta ctagatgcat cactgggtgt    2940
tgatcttaca agatattgat gataacactt aaaattgtaa cctgcatttt tcactttgct    3000
ctcaattaaa gtctattcaa aaggaaaaaa aaaaaaa                              3037
```

<210> SEQ ID NO 2
<211> LENGTH: 1401
<212> TYPE: DNA
<213> ORGANISM: Homo sapiens

<400> SEQUENCE: 2

```
ggctgggact ggctgagcct ggcgggaggc ggggtccgag tcaccgcctg ccgccgcgcc      60
cccggtttct ataaattgag cccgcagcct cccgcttcgc tctctgctcc tcctgttcga    120
cagtcagccg catcttcttt tgcgtcgcca gccgagccac atcgctcaga caccatgggg    180
aaggtgaagg tcggagtcaa cggatttggt cgtattgggc gcctggtcac cagggctgct    240
tttaactctg gtaaagtgga tattgttgcc atcaatgacc ccttcattga cctcaactac    300
atggtttaca tgttccaata tgattccacc catggcaaat tccatggcac cgtcaaggct    360
gagaacggga agcttgtcat caatggaaat cccatcacca tcttccagga gcagatccc    420 tccaaaatca gtggggcga tgctggcgct gagtacgtcg tggagtccac tggcgtcttc    480
accaccatgg agaaggctgg ggctcatttg caggggggag ccaaaagggt catcatctct    540 gcccctctg ctgatgcccc catgttcgtc atgggtgtga accatgagaa gtatgacaac    600
agcctcaaga tcatcagcaa tgcctcctgc accaccaact gcttagcacc cctggccaag    660
gtcatccatg acaactttgg tatcgtggaa ggactcatga ccacagtcca tgccatcact    720
gccacccaga agactgtgga tggccctcc gggaaactgt ggcgtgatgg ccgcggggct    780
ctccagaaca tcatccctgc ctctactggc gctgccaagg ctgtgggcaa ggtcatccct    840
gagctgaacg ggaagctcac tggcatggcc ttccgtgtcc ccactgccaa cgtgtcagtg    900
gtggacctga cctgccgtct agaaaaacct gccaaatatg atgacatcaa gaaggtggtg    960
aagcaggcgt cggagggccc cctcaagggc atcctgggct acactgagca ccaggtggtc    1020
tcctctgact tcaacagcga cacccactcc tccacctttg acgctgggc tggcattgcc    1080 ctcaacgacc actttgtcaa gctcatttcc tggtatgaca cgaatttgg ctacagcaac    1140 agggtggtgg acctcatggc ccacatggcc tccaaggagt aagaccctg gaccaccagc    1200 cccagcaaga gcacaagagg aagagagaga ccctcactgc tggggagtcc ctgccacact    1260
cagtccccca ccacactgaa tctcccctcc tcacagttgc catgtagacc ccttgaagag    1320
gggaggggcc tagggagccg caccttgtca tgtaccatca ataaagtacc ctgtgctcaa    1380
ccaaaaaaaa aaaaaaaaa a                                                1401
```

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
   (A1) Forward Primer

<400> SEQUENCE: 3

```
cgctattcgc aatcagggtt ac                                                22
```

<210> SEQ ID NO 4
<211> LENGTH: 22

```
<212> TYPE: DNA
<213> ORGANISM: Artificial Sequence
<220> FEATURE:
<223> OTHER INFORMATION: Description of Artificial Sequence: Synthetic
      (A2) Reverse Primer

<400> SEQUENCE: 4
ggatcctcat gcttgaatga gt                                            22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      (A3) Probe

<400> SEQUENCE: 5
agcacggtca ccttcgacgg ga                                            22

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
      (a1) Forward Primer

<400> SEQUENCE: 6
cagccgagcc acatcg                                                   16

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      (a2) Reverse Primer

<400> SEQUENCE: 7
gtcaatgaag gggtcattga tg                                            22

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      (a3) Probe

<400> SEQUENCE: 8
ttggtcgtat tgggcgcctg g                                             21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      (B1) Forward Primer

<400> SEQUENCE: 9
gataaccaca caacgcccat c                                             21

<210> SEQ ID NO 10
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      (B2) Reverse Primer

<400> SEQUENCE: 10
cacacgtcgc acatcctgaa t                                              21

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      (B3) Probe

<400> SEQUENCE: 11
aatacacacg cacggtgtct tcagag                                         26

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      (b2) Reverse Primer

<400> SEQUENCE: 12
tgatggcaac aatatccact ttacc                                          25

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      Forward Primer

<400> SEQUENCE: 13
ccgcatcttc ttttgcgtc                                                 19
```

QUANTIFICATION METHOD FOR EXPRESSION LEVEL OF WT1 MRNA

SEQUENCE LISTING

The instant application contains a Sequence Listing which has been submitted electronically in ASCII format and is hereby incorporated by reference in its entirety. Said ASCII copy, created on Jun. 23, 2016, is named 04676_0337_SL.txt and is 8,917 bytes in size.

TECHNICAL FIELD

The present invention relates to a novel method for quantifying the expression level of human WT1 mRNA that can be used for diagnosing cancer, such as leukemia and solid cancer, or for determining when to perform bone marrow transplantation.

BACKGROUND ART

Wilms tumor gene-1 ("WT1") is a gene that was identified as a causative gene of pediatric Wilms tumor by Call et al. in 1990 (Non-patent Literature 1). Thereafter, it has been indicated that WT1 mRNA is expressed at a high rate in not only pediatric Wilms tumor but also solid cancer cells, such as solid cancer cell lines, e.g., gastric cancer cell lines, colon cancer cell lines, lung cancer cell lines, and breast cancer cell lines (Non-patent Literature 2). The WT1 gene is now considered to be a cancer-related gene associated not only with pediatric Wilms tumor but also many cancers.

Call et al. report the expression of WT1 mRNA in K562 cells and CCRF-CEM cells, which are both leukemia cell lines (see Non-patent Literature 1). Miwa et al. report that WT1 mRNA was expressed in 15 of 22 cases of acute myeloid leukemia ("AML") in northern blot analysis (Non-patent Literature 3). Further, Inoue et al. report that the expression of WT1 mRNA was observed in 100% (45/45) or cases at the first medical examination for AML (Non-patent Literature 4). In addition, it is reported that the expression level of WT1 mRNA at diagnosis is associated with prognosis (Non-patent Literature 5), that even if the expression of WT1 mRNA returns to normal levels with treatment, it increases again when recurrence occurs (Non-patent Literature 6), and that the expression level of WT1 mRNA at recurrence is higher than at diagnosis (Non-patent Literature 7).

The WT1 gene has been sold as an extracorporeal diagnostic pharmaceutical product that is useful as a new marker for monitoring minimal residual disease (or "MRD") in the treatment for AML because of the fact that the WT1 gene appears with high frequency as a single gene in patients with AML and the expression of the WT1 gene increases again at recurrence after return to normal levels with treatment.

A hitherto-known method for measuring human WT1 mRNA is a competitive quantification method using β-actin as a standard (Patent Literature 1). However, this method requires not only measuring WT1 mRNA and β-actin mRNA separately, but also performing extension reactions after a reverse transcription reaction is done, i.e., two-step RT-PCR, thus requiring a lot of time.

As another method for measuring human WT1 mRNA, Patent Literature 2 discloses one-step RT-PCR for WT1 mRNA. However, this method requires the expression level of a housekeeping gene used for correcting the expression level of the WT1 gene to be separately measured, and thus is complicated.

CITATION LIST

Patent Literature

PTL 1: JPH11-089599A
PTL 2: JPH11-039596A

Non-Patent Literature

NPL 1: Call, K. M. et al., Cell 1990; 60: 509-520.
NPL 2: Jpn. J. Cancer Res. 1999; 90: 194-204.
NPL 3: Miwa, H., et al., Leukemia 1992; 6: 405-409.
NFL 4: Inoue, K., et al., Blood, 1994, 84(9), 3071-3079.
NPL 5: Blood 1997; 90: 1217-1225.
NPL 6: Blood 1996; 88: 2267-2278.
NPL 7: Blood 1996; 88: 4396-4398.

SUMMARY OF INVENTION

Technical Problem

As described above, known methods for quantifying the expression level of the WT1 gene are problematic in that they require a lot of time and are complicated. Accordingly, there is a need for a method that can quantify the expression level of the human WT1 gene conveniently and in a short period of time. Therefore, an object of the present invention is to provide a novel method for quantifying WT1 mRNA conveniently and in a short period of time. In particular, an object of the present invention is to provide a novel method that enables WT1 mRNA to be quantified conveniently and in a short period of time by simultaneously quantifying both the expression level of human WT1 mRNA and the expression level of a housekeeping gene.

Solution to Problem

The present inventors conducted extensive research to achieve the above object and found that the expression level of human WT1 mRNA of interest can be quantified conveniently and in a short period of time by simultaneously subjecting human WT1 gene (mRNA), which is a gene of interest, and a housekeeping gene (mRNA), which is a gene for correction, to reverse transcription and extension reactions carried oat sequentially in the same vessel (one step). The inventors confirmed that this one-step RT-PCR enables a gene of interest to be detected with higher sensitivity in a more convenient manner than two-step RT-PCR, which amplifies a gene of interest and a gene for correction separately, and in a time period almost as short.

The present invention has been accomplished based on the above finding and includes the following embodiments.
(I) Method for Quantifying the Expression Level of Human WT1 mRNA
(I-1) A method for quantifying the expression level of human WT1 mRNA by one-step RT-PCR, the method comprising simultaneously subjecting the human WT1 mRNA and a housekeeping gene (mRNA) to reverse transcription and extension reactions carried out sequentially in the same vessel.
(I-2) The method according to (I-1), wherein the housekeeping gene is GAPDH mRNA.
(I-3) The method according to (I-1) or (I-2), wherein
(a) a primer set comprising a forward PCR primer consisting of the base sequence set forth in SEQ ID NO: 3 and a reverse PCR primer consisting of the base sequence set forth in SEQ ID NO: 4, or (b) a primer set comprising a forward PCR primer consisting of the base sequence set forth in SEQ ID NO: 9 and a reverse PCR primer consisting of the base sequence set form in SEQ ID NO: 10 is used for PCR amplification of the human WT1 mRNA.

(I-4) The method according to (I-1) or (I-2), wherein (a') a primer set comprising a forward PCR primer consisting of the base sequence set forth in SEQ ID NO: 3 and a reverse PCR primer consisting of the base sequence set forth in SEQ ID NO: 4, and a probe consisting of the base sequence set forth in SEQ ID NO: 5, the probe being labeled, or (b') a primer set comprising a forward PCR primer consisting of the base sequence set forth in SEQ ID NO: 9 and a reverse PCR primer consisting of the base sequence set forth in SEQ ID NO: 10, and a probe consisting of the base sequence set forth in SEQ ID NO: 11, the probe being labeled are used for PCR amplification of the human WT1 mRNA.

(I-5) The method according to (I-3) or (I-4), wherein (c) a primer set comprising a forward PCR primer consisting of the base sequence set forth in SEQ ID NO: 6 and a reverse PCR primer consisting of the base sequence set forth in SEQ ID NO: 7 or 12 is further used for PCR amplification of the human WT1 mRNA.

(I-6) The method according to (I-3) or (I-4), wherein (c') a primer set comprising a forward PCR primer consisting of the base sequence set forth in SEQ ID NO: 6 and a reverse PCR primer consisting of the base sequence set forth in SEQ ID NO: 7 or 12, and a probe consisting of the base sequence set forth in SEQ ID NO: 8, the probe being labeled, are further used for PCR amplification of the human WT1 mRNA.

(II) Kit for Real-Time PCR for Quantifying the Expression Level of Human WT1 mRNA (II-1) A kit for real-time PCR for quantifying the expression level of human WT1 mRNA, the kit comprising (a) a primer set comprising a forward PCR primer consisting of the base sequence set forth in SEQ ID NO: 3 and a reverse PCR primer consisting of the base sequence set forth in SEQ ID NO: 4, or (b) a primer set comprising a forward PCR primer consisting of the base sequence set forth in SEQ ID NO: 9 and a reverse PCR primer consisting of the base sequence set forth in SEQ ID NO: 10.

(II-2) A kit for real-time PCR for quantifying the expression level of human WT1 mRNA, the kit comprising (a') a primer set comprising a forward PCR primer consisting of the base sequence set forth in SEQ ID NO: 3 and a reverse PCR primer consisting of the base sequence set forth in SEQ ID NO: 4, and a probe consisting of the base sequence set forth in SEQ ID NO: 5, the probe being labeled, or (b') a primer set comprising a forward PCR primer consisting of the base sequence set forth in SEQ ID NO: 9 and a reverse PCR primer consisting of the base sequence set forth in SEQ ID NO: 10, and a probe consisting of the base sequence set forth in SEQ ID NO: 11, the probe being labeled.

(II-3) The kit for real-time PCR for quantifying the expression level or human WT1 mRNA according to (II-1) or (II-2), further comprising (c) a primer set comprising a forward PCR primer consisting of the base sequence set forth in SEQ ID NO: 6 and a reverse PCR primer consisting of the base sequence set forth in SEQ ID NO: 7 or 12.

(II-4) The kit for real-time PCR for quantifying the expression level of human WT1 mRNA according to (II-1) or (II-2), further comprising (c') a primer set comprising a forward PCR primer consisting of the base sequence set forth in SEQ ID NO: 6 and a reverse PCR primer consisting of the base sequence set forth in SEQ ID NO: 7 or 12, and a probe consisting of the base sequence set forth in SEQ ID NO: 8, the probe being labeled.

Advantageous Effects of Invention

The present invention makes it possible to provide a method for quantifying the expression level of WT1 mRNA by using a simpler operation, with less effort, and in a shorter period of time than with hitherto-known methods for quantifying the expression level of WT1 mRNA. Additionally, the method of the present invention enables detection with higher sensitivity than hitherto-known measurement methods that use two-step RT-PCR. More specifically, the expression level of human WT1 mRNA can be quantified conveniently, in a short period of time, and with high sensitivity by using the method or kit for real-time PCR of the present invention.

The expression level of human WT1 mRNA thus quantified is a useful index for diagnosing onset and recurrence of leukemia or solid cancer, determining prognosis of leukemia or solid cancer, and determining when to perform bone marrow transplantation.

Figure 1:
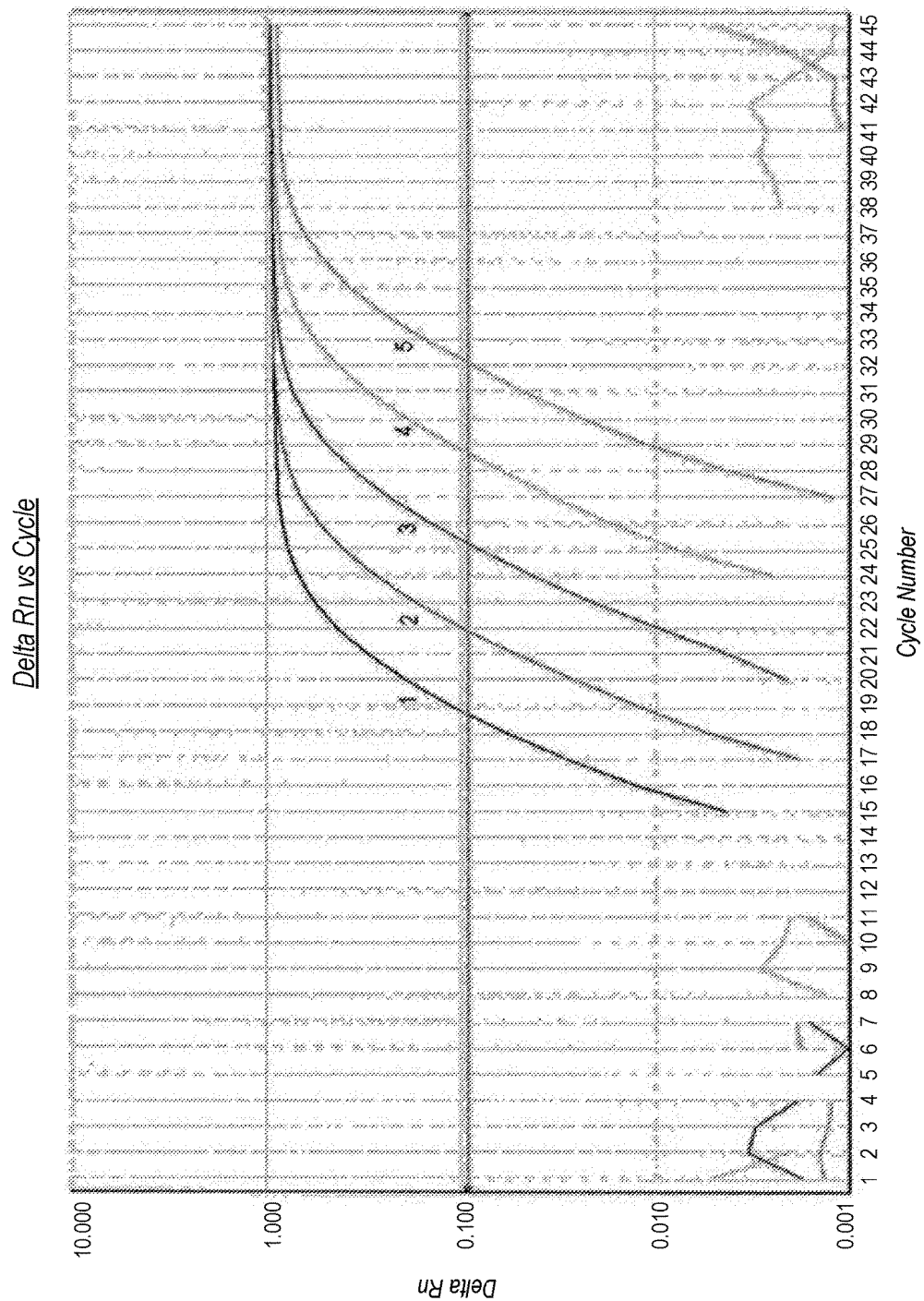
FIG. 1 shows WT1 mRNA amplification curves for various concentrations (in the graph, 1: $2.5 \times 10^5$ copies/test, 2: $2.5 \times 10^4$ copies/test, 3: $2.5 \times 10^3$ copies/test 4: $2.5 \times 10^2$ copies/test, and 5: $2.5 \times 10^1$ copies/test) of the WT1 RNA standard when WT1 mRNA was amplified alone (Example 1).

DESCRIPTION OF EMBODIMENTS (I) Method for Quantifying the Expression Level of Human WT1 mRNA The method of the present invention is a method for quantifying the expression level of human WT1 mRNA by one-step RT-PCR.

The human WT1 gene to be measured in the present invention is a gene that consists of 3037 bp and that is identified as a causative gene of pediatric Wilms tumor as described above. The human WT1 gene is registered with the NCBI as "*Homo sapiens* Wilms tumor 1 (WT1), transcript variant D, mRNA" (NM_024426.4). The base sequence of the human WT1 gene is shown in SEQ ID NO: 1 in the sequence listing.

The test sample to be measured in the method of the present invention is not particularly limited as long as it contains the human WT1 mRNA mentioned above. Examples of usable test samples include total RNA or mRNA-enriched samples obtained by treating a sample that may contain WT1 mRNA by known method, for example, a biological sample, such as human-derived cells, tissue, blood, sputum, feces, urine, and the like. Such RNA samples may be used in the form of aqueous solutions or in the state in which they are adsorbed or immobilized to an appropriate solid phase. It is suitable that the total RNA amount is 0.01 ng to 1 μg per 100 μl of a reaction mixture.

Housekeeping genes are genes that are always expressed in all cells irrespective of cell differentiation and that play an essential role in the survival of cells although they do not perform specialized functions. Examples include genes encoding RNA synthetases, energy metabolizing enzymes, ribosomal proteins, cytoskeletal proteins, etc. Specific examples include genes encoding glyceraldehyde-3-phosphate dehydrogenase (GAPDH), β-actin, β2-microglobulin, hypoxanthine phosphoribosyltransferase 1 (HPRT 1), etc. The housekeeping gene used in the present invention is preferably a gene that does not compete with the human WT1 gene to be measured in amplification by RT-PCR; for example, it is preferably a gene that has a low bass sequence homology to the human WT1 gene. The housekeeping gene is preferably GAPDH gene.

GAPDH gene is a gene registered with the NCBI as "*Homo sapiens* glyceraldehyde-3-phosphate dehydrogenase (GAPDH), mRNA" (NM_002046.3). The base sequence of GAPDH is shown in SEQ ID NO: 2 in the sequence listing.

The reaction buffer used for one-step RT-PCR (reverse transcription and extension reactions) in the present invention may be a water-soluble buffer suitable for an enzyme having reverse transcription activity to show the activity, and is, for example, a buffer with a pH of 7 to 10, and preferably a pH of 8 to 9. Examples of such buffers include tris buffers. Further, the buffer may contain various ions necessary for the activity of an enzyme having reverse transcription activity or DNA polymerase. Among them, Na ions and K ions may be individually added in the form of salt at a concentration of 5 to 50 mM. Mg ions may be added in the form of salt at a concentration of 1 to 10 mM. If necessary, the buffer may contain an agent that promotes or stabilizes the activity of an enzyme having reverse transcription activity or DNA polymerase, such as a surfactant, bovine serum albumin (BSA), or gelatin. In addition, a ribonuclease inhibitor may be added to inhibit the degradation of RNA and RNA competitor in the sample.

Examples of enzymes having reverse transcription activity include avian myeloblastosis virus-derived reverse transcriptase (AMV), Rous-associated virus-derived reverse transcriptase (RAV2), Moloney murine leukemia virus-derived reverse transcriptase (MMLV), *Thermus thermophilus*-derived DNA polymerase (Tth), *Bacillus caldotenax*-derived DNA polymerase (Bca), and derivatives thereof. Among these, Tth is most suitable for the present invention. Specific examples of Tth include DNA polymerases of thermostable enzymes derived from *Thermus* species Z05. These enzymes may be obtained by purification from their original sources or recombinant proteins produced by using genetic engineering techniques.

Four deoxynucleotide triphosphates (dATP, dCTP, dGTP, and dTTP; in the present specification, these four deoxynucleotide triphosphates may be collectively referred to as "dNTPs") as substrates in cDNA synthesis and PCR are added to the reaction mixture. All or a portion of dNTPs may be modified and/or replaced with labeled dNTPs within the range that allows extension of a DNA strand synthesized from a primer.

The primers used in cDNA synthesis (reverse transcription and extension reactions) from the target RNA in the present invention are oligonucleotides having a base sequence complementary to at least the base sequence of the target RNA, and need to anneal to the target RNA in the reaction conditions employed. Such oligonucleotides have a length of, for example, 6 to 100 nucleotides, and preferably 10 to 30 nucleotides. Modified and/or labeled primers can also be used. The primers can be chemically synthesized by, for example, a known method. The primers used in PCR needs to allow at least amplification of DNA using cDNA derived from the target RNA as a template. Thus, the primers are oligonucleotides having a base sequence complementary to at least the base sequence of the template cDNA, and need to anneal to the cDNA in the reaction conditions employed. Such oligonucleotides preferably function as primers for DNA amplification using cDNA as a template as well as primers for synthesis of cDNA from the target RNA mentioned above (reverse transcription and extension reactions).

Examples of the primer set suitably used for reverse transcription of human WT1 mRNA, which is a gene of interest of the present invention, into cDNA, extension, and amplification include a primer set A comprising (A1) forward primer and (A2) reverse primer shown in Table 1 and a primer set B comprising (B1) forward primer and (B2) reverse primer shown in Table 2. Tables 1 and 2 also show sequence-specific binding probes ((A3) probe and (B3) probe) used for detecting amplification products of the human WT1 gene amplified with these primer sets. These probes are preferably labeled to facilitate detection of the amplification products.

Examples of the primer set suitably used for reverse transcription of human GAPDH mRNA, which is suitably used as a housekeeping gene in the method of the present invention, into cDNA, extension, and amplification include a primer set A comprising (a1) forward primer and (a2) reverse primer shown in Table 1 and a primer set B comprising (b1) forward primer and (b2) reverse primer shown in Table 2. Tables 1 and 2 also show sequence-specific binding probes ((a3) probe and (b3) probe) used for detecting amplification products of the human GAPDH gene amplified with these primer sets. These probes are preferably labeled to facilitate detection of the amplification products.

As methods for labeling a probe, there are RI methods and non-RI methods. It is preferable that a non-RI method be used. Examples of non-RI methods include fluorescence labeling methods, biotinylation methods, chemiluminescence methods, and the like. It is preferable that a fluorescence labeling method be used. There is no particular limitation on the fluorescent substance as long as the substance can bind to a base moiety of a nucleic acid. A cyanine dye (such as Cy3 or Cy5 in the Cy Dye™ series), a Rhodamine 6G reagent, N-acetoxy-N2-acetylaminofluorene, a iodine derivative thereof, or the like can be used.

mRNA to be measured, and a housekeeping gene (e.g., GAPDH mRNA) are added to the vessel, and the mixture is reacted multiple times at 50 to 70° C., and preferably 55 to 65° C., for about 2 to about 30 minutes, and preferably about 2 to about 10 minutes to synthesize cDNA (reverse tran-

TABLE 1

Sequence Set A

| Gene | Primer | | Corresponding Gene Region | Sequence Set A | SEQ ID NO |
|---|---|---|---|---|---|
| WT1 | (A1) | Forward | 820-841* | CGCTATTCGCAATCAGGGTTAC | 3 |
| | (A2) | Reverse | 936-915* | GGATCCTCATGCTTGAATGAGT | 4 |
| | (A3) | Probe | 842-863* | AGCACGGTCACCTTCGACGGGA | 5 |
| GAPDH | (a1) | Forward | 77-92** | CAGCCGAGCCACATCG | 6 |
| | (a2) | Reverse | 219-198** | GTCAATGAAGGGGTCATTGATG | 7 |
| | (a3) | Probe | 134-154** | TTGGTCGTATTGGGCGCCTGG | 8 |

A single asterisk indicates a region of the human WT1 gene (NM_024426.4: SEQ ID NO: 1).
Double asterisks indicate a region of the human GAPDH gene (NM_002046.3): SEQ ID NO: 2).

TABLE 2

Sequence Set B

| Gene | Primer | | Corresponding Gene Region | Sequence Set B | SEQ ID NO |
|---|---|---|---|---|---|
| WT1 | (B1) | Forward | 1214-1234* | GATAACCACACAACGCCCATC | 9 |
| | (B2) | Reverse | 1303-1283* | CACACGTCGCACATCCTGAAT | 10 |
| | (B3) | Probe | 1255-1280* | AATACACACGCACGGTGTCTT CAGAG | 11 |
| GAPDH | (b1) | Forward | 77-92** | CAGCCGAGCCACATCG | 6 |
| | (b2) | Reverse | 202-178** | TGATGGCAACAATATCCACTTT ACC | 12 |
| | (b3) | Probe | 134-154** | TTGGTCGTATTGGGCGCCTGG | 8 |

A single asterisk indicates a region of the human WT1 gene (NM_024426.4: SEQ ID NO: 1).
Double asterisks indicate a region of the human GAPDH gene (NM_002046.3): SEQ ID NO: 2).

The RNA standards used in the present invention can be prepared by a known method. For example, the RNA standards can be prepared with reference to the description of "Proceedings of the Rational Academy of Sciences of the United States of America" (Proc. Natl. Acad. Sci. USA), Vol. 87, pp. 2725 to 2729 (1990), "Clinical Chemistry (Clin. Chem.)," Vol. 41, pp. 819 to 825 (1995), "Blood," Vol. 82, pp. 1929 to 1936 (1993), or the like.

The details are as follows. A promoter sequence that serves as an origination of a reaction of an RNA synthetase, such as T7 RNA polymerase, is added to a double-stranded DNA sequence to be amplified, thereby preparing a DNA sequence used as a template for RNA synthesis. An RNA polymerase, the double-stranded DNA comprising the RNA promoter sequence, and nucleoside triphosphates are added to a reaction vessel, and a reaction is performed at 37° C. for 30 minutes to 2 hours to synthesize single stranded RNA that is complementary to the template DNA downstream of the RNA promoter.

There is no limitation on the reaction procedure and reaction conditions of the one-step RT-PCR used in the present invention. The following is an example.

For example, a reaction mixture containing dNTPs, Mg salt, a ribonuclease inhibitor, an enzyme having reverse transcription activity, primers, and the like is added to a reaction vessel and kept cool at 4° C. or lower until the start of reaction. A test sample that can contain human WT1 scription reaction). Immediately afterward, heating at 90 to 99° C. for about 10 seconds to about 2 minutes is performed to denature the RNA-cDNA complex (heat denaturation). Further, 2 to 50 cycles of temperature reaction, each consisting of heat denaturation at 90 to 99° C., an annealing reaction at 45 to 65° C., and a DNA extension reaction at 60 to 80° C., are performed, thereby amplifying the DNA fragment derived from the target RNA. Further, when nested PCR is performed to improve sensitivity and/or specificity, primers used in the first PCR and primers used in the second PCR may be added together to a reaction vessel from the beginning, and two-stage PCR may be performed in a successive manner. In this case, the amount of the primers for the first PCR is required to be less than the amount of the primers for the second PCR, and it is suitable that the amount of the primers for the first PCR is preferably 100 times less than the amount for the second PCR, or smaller.

The method described above for the present invention not only makes it possible to conveniently measure the expression level of human WT1 mRNA by one-step RT-PCR in the same vessel, but also enables detection with higher sensitivity than two-step RT-PCR, which performs RT-PCR for a gene of interest and RT-PCR for a housekeeping gene separately, as shown in Example 2. In other words, the method of the present invention enables highly accurate detection even when the concentration of human WT1 mRNA expressed in a sample is low.

This method can be performed more conveniently by using the real-time PCR kit described below.

(II) Kit for Real-Time PCR for Quantifying the Expression Level of Human WT1 mRNA The reagent kit for RT-PCR of the present invention comprises both a primer set for subjecting human WT1 mRNA to RT-PCR and a primer set for subjecting a housekeeping gene, preferably GAPDH mRNA, to RT-PCR. The kit may also comprise probes used for detecting amplification products of human WT1 mRNA amplified by RT-PCR and amplification products of the housekeeping gene amplified by RT-PCR.

An example of the kit is one that comprises a primer set A comprising (A1) forward primer (SEQ ID NO: 3) and (A2) reverse primer (SEQ ID NO: 4) shown in Table 1 as a primer set for subjecting human WT1 mRNA to RT-PCR, as well as (A3) probe (SEQ ID NO: 5) shown in Table 1 as a sequence-specific binding probe used for detecting amplification products of human WT1 gene amplified with this primer set, and that also comprises a primer set A comprising (a1) forward primer (SEQ ID NO: 6) and (a2) reverse primer (SEQ ID NO: 7) shown in Table 1 as a primer set for subjecting human GAPDH mRNA suitably used as a housekeeping gene to RT-PCR, as well as (a3) probe (SEQ ID NO: 8) shown in Table 1 as a sequence-specific binding probe used for detecting amplification products of human GAPDH gene amplified by this primer set.

The probes are preferably labeled to facilitate detection of the amplification products.

As methods for labeling a probe, there are RI methods and non-RI methods. It is preferable that a non-RI method be used. Examples of non-RI methods include fluorescence labeling methods, biotinylation methods, chemiluminescence methods, and the like. It is preferable that a fluorescence labeling method be used. There is no particular limitation on the fluorescent substance as long as the substance can bind to a base moiety of a nucleic acid. A cyanine dye (such as Cy3 or Cy5 in the Cy Dye™ series), a Rhodamine 6G reagent, N-acetoxy-N2-acetylaminofluorene, a iodine derivative thereof, or the like can be used.

Another example of the kit is one that comprises a primer set B comprising (B1) forward primer (SEQ ID NO: 9) and (B2) reverse primer (SEQ ID NO: 10) shown in Table 2 as a primer set for subjecting human WT1 mRNA to RT-PCR, as well as (B3) probe (SEQ ID NO: 11) shown in Table 2 as a sequence-specific binding probe used for detecting amplification products of the human WT1 gene amplified with this primer set, and that also comprises a primer set B comprising (b1) forward primer (SEQ ID NO: 6) and (b2) reverse primer (SEQ ID NO: 12) shown in Table 2 as a primer set for subjecting human GAPDH mRNA suitably used as a housekeeping gene to RT-PCR, as well as (b3) probe (SEQ ID NO: 8) shown in Table 2 as a sequence-specific binding probe used for detecting amplification products of the human GAPDH gene amplified with this primer set.

The kit for RT-PCR of the present invention may comprise not only the above components but also various components necessary for two reactions, i.e., a reverse transcription reaction and PCR, (dNTPs, Mg salt, buffering component for pH adjustment, etc.), and an enzyme having reverse transcription activity. The kit may further comprise a component for stabilizing an enzyme, a ribonuclease inhibitor, etc.

The reactions can be started by only placing a requisite amount of the reaction mixture in a suitable reaction vessel and adding a sample to be measured. Thus, the expression level of human WT1 mRNA can be conveniently quantified. In particular, it is useful in quantifying the expression level of human WT1 mRNA in multiple test samples. In addition, operation efficiency can be further improved by preparing beforehand a reaction vessel in which a requisite amount of the reaction mixture for one time is dispensed. According to the method described above, the kit for RT-PCR of the present invention allows for convenient and rapid quantification of the expression level of human WT1 mRNA with no cross contamination problems. Examples of the kit include a kit comprising various reagents used for the method, a kit comprising the reaction mixture used in the present invention, a kit comprising a reaction vessel in which the amount of the reaction mixture for one time is dispensed, and the like. The kit is particularly useful as a kit for various tests, in particular as a kit for clinical diagnosis. The kit can be widely used in examination for leukemia, examination for micrometastasis of solid cancer, examination for minimal residual disease, examination for infectious disease, and the like.

EXAMPLES

Examples are given below to illustrate the present invention in more detail; however, the present invention is not limited to these Examples.

Example 1

Measurement by One-Step and Multiplex RT-PCR
(1) Design of Primers and Probes

Human WT1 mRNA was selected as a gene of interest to be measured, and GAPDH mRNA was selected as an endogenous control gene (gene for correction) for correcting the expression level of the gene to be measured. Primer sets and probes that allow for specific amplification and detection of the individual genes were designed and synthesized.

Fluorescently labeled probes were prepared to detect the gene of interest (human WT1 mRNA) and the gene for correction (GAPDH mRNA) simultaneously as follows. The 5' end of the probe for detecting the gene of interest was labeled with FAM (6-carboxyfluorescein), and the 5' end of the probe for detecting the gene for correction was labeled with HEX (6-hexachlorofluorescein). The 3' end of each probe was labeled with ATTO-540Q (ATTO-TEC GmbH) as a quenching dye.

Table 3 shows the sequences of the primers and probes used in the Examples.

TABLE 3

| Gene | Primer | Sequence Set A | Sequence Set B |
|---|---|---|---|
| WT1 | Forward | SEQ ID NO: 3<br>CGCTATTCGCAATCAGGGTTAC | SEQ ID NO: 9<br>GATAACCACACAACGCCCATC |
|  | Reverse | SEQ ID NO: 4<br>GGATCCTCATGCTTGAATGAGT | SEQ ID NO: 10<br>CACACGTCGCACATCCTGAAT |

TABLE 3-continued

| Gene | Primer | Sequence Set A | Sequence Set B |
|------|--------|----------------|----------------|
|  | Probe | SEQ ID NO: 5<br>AGCACGGTCACCTTCGACGGGA | SEQ ID NO: 11<br>AATACACACGCACGGTGTCTTCAGAG |
| GAPDH | Forward | SEQ ID NO: 6<br>CAGCCGAGCCACATCG | SEQ ID NO: 6<br>CAGCCGAGCCACATCG |
|  | Reverse | SEQ ID NO: 7<br>GTCAATGAAGGGGTCATTGATG | SEQ ID NO: 12<br>TGATGGCAACAATATCCACTTTACC |
|  | Probe | SEQ ID NO: 8<br>TTGGTCGTATTGGGCGCCTGG | SEQ ID NO: 8<br>TTGGTCGTATTGGGCGCCTGG |

(2) Preparation of Standards (WT1 mRNA and GAPDH mRNA)

Standards were prepared as follows. RNA was extracted from leukemia cell line K562 expressing WT1 mRNA and GAPDH mRNA, and RT-PCR was performed by using the RNA as a template and using primers complementary to the base sequences of WT1 mRNA and primers complementary to the base sequences of GAPDH mRNA, thereby obtaining the base sequence of part of WT1 mRNA and the base sequence of part of GAPDH mRNA. The thus-obtained WT1 mRNA sequence and GAPDH mRNA sequence were cloned into a pT7blue plasmid vector and transformed into $E.\ coli$ strain DH5α. The transformed $E.\ coli$ was then cultured, and plasmid DNA was extracted. A sequence following a portion in which the WT1 mRNA sequence and the GAPDH mRNA sequence were inserted in the plasmid DNA was cleaved with restriction enzyme RcoRI to obtain linear DNA. The RNA sequences of WT1 mRNA and GAPDH mRNA were synthesized with T7 RNA polymerase, which is an enzyme that recognizes the T7 promoter sequence in plasmid DNA and that synthesizes RNA using DNA as a template. The synthesized RNA was diluted with a TE buffer containing 50 ng/μL of $E.\ coli$ transfer RNA to prevent non-specific adsorption to a reaction vessel, thereby preparing RNA standards of the genes (WT1 and GAPDH).

The concentration of the thus-prepared WT1 RNA standard was adjusted to $2.5 \times 10^1$, $2.5 \times 10^2$, $2.5 \times 10^3$, $2.5 \times 10^4$, and $2.5 \times 1^5$ copies/test. The concentration of the thus-prepared GAPDH RNA standard was adjusted to $1.0 \times 10^4$, $1.0 \times 10^5$, $1.0 \times 10^6$, $1.0 \times 10^7$, and $1.0 \times 10^8$ copies/test.

(3) RT-PCR Reaction

RT-PCR was performed by one-step RT-PCR in which a reverse transcription reaction and PCR are conducted sequentially in a single tube.

(3-1) Reverse Transcriptase

Z05 DNA polymerase (thermostable enzyme from $Thermus$ species Z05: Roche Diagnostics) was used.

(3-2) Reaction Conditons (a) Reverse Transcription Reaction and PCR Reaction

A reverse transcription reaction was performed for a total of 15 minutes, i.e., 5 minutes at 55° C., 5 minutes at 60° C., and 5 minutes at 65° C. PCR was then performed under the following conditions: heat denaturation at 92° C. for 15 seconds, annealing at 60° C. for 40 seconds, and a DNA extension reaction repeated for 45 cycles.

(b) Reagent Concentration

The volume of the reaction mixture was 20 μL. The primer concentration in the reaction mixture was such that the forward primer final concentration and the reverse primer final concentration were 0.2 μM. The probe final concentration was 0.1 μM.

(3-3) Reaction/Measurement Apparatus

RT-PCR was per formed using an Applied Biosystems 7500 Fast Realtime PCR system (Life Technologies).

(4) Results (4-1) Confirmation of Fluorescence Amplification Curves

Fluorescence amplification curves and the number of amplification cycles (a) for the WT1 RNA standard when WT1 mRNA was amplified alone, (b) for the GAPDH RNA standard when GAPDH mRNA was amplified alone, and (c) for the WT1 RNA standard and the GAPDH RNA standard when WT1 mRNA and GAPDH mRNA were amplified simultaneously were confirmed.

Figure 2:
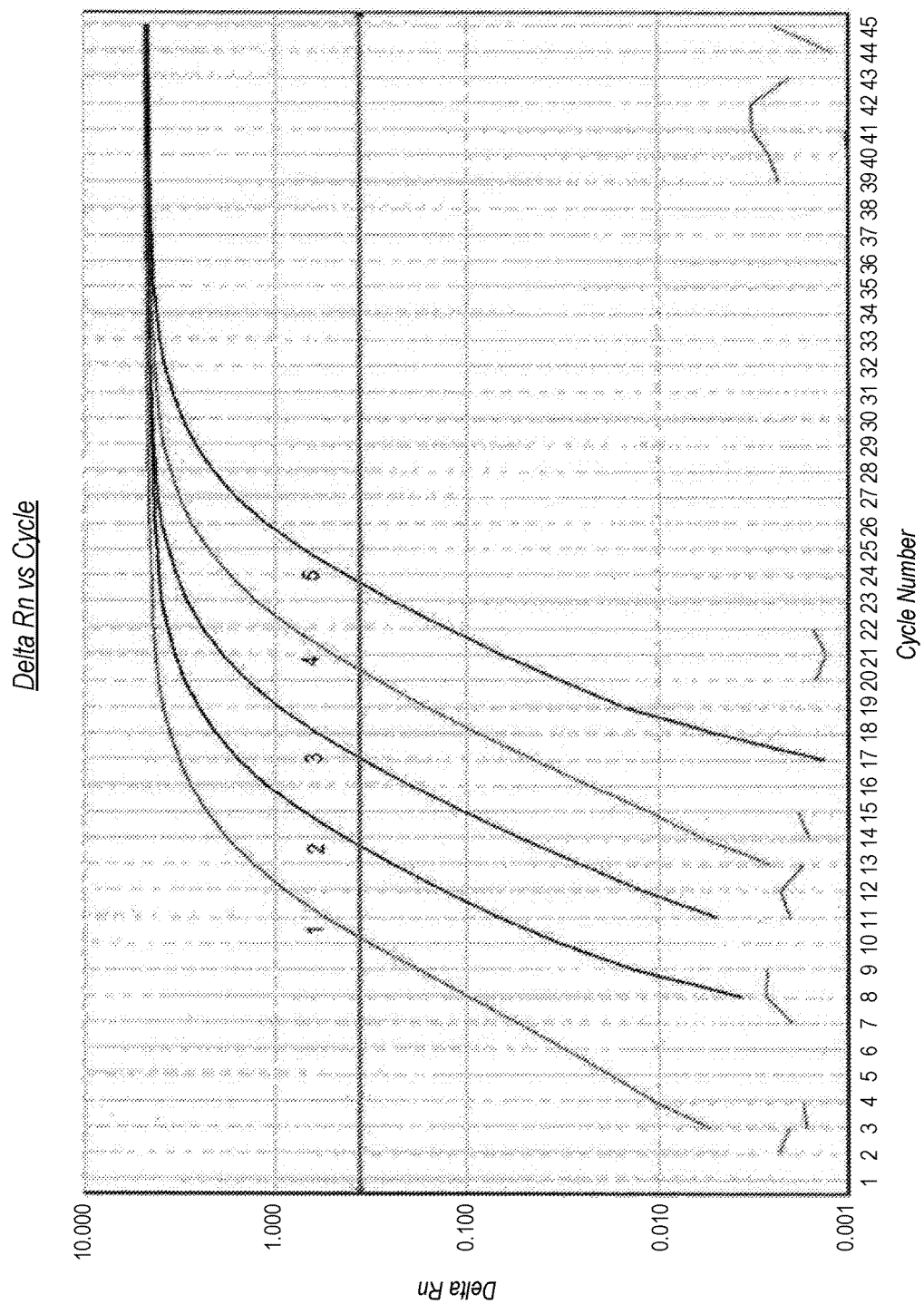
FIG. 2 shows GAPDH mRNA amplification curves for various concentrations (in the graph, 1: $1.0 \times 10^8$ copies/test, 2: $1.0 \times 10^7$ copies/test, 3: $1.0 \times 10^6$ copies/test, 4: $1.0 \times 10^5$ copies/test, and 5: $1.0 \times 10^4$ copies/test) of the GAPDH RNA standard when GAPDH mRNA was amplified alone (Example 1).
Figure 3:
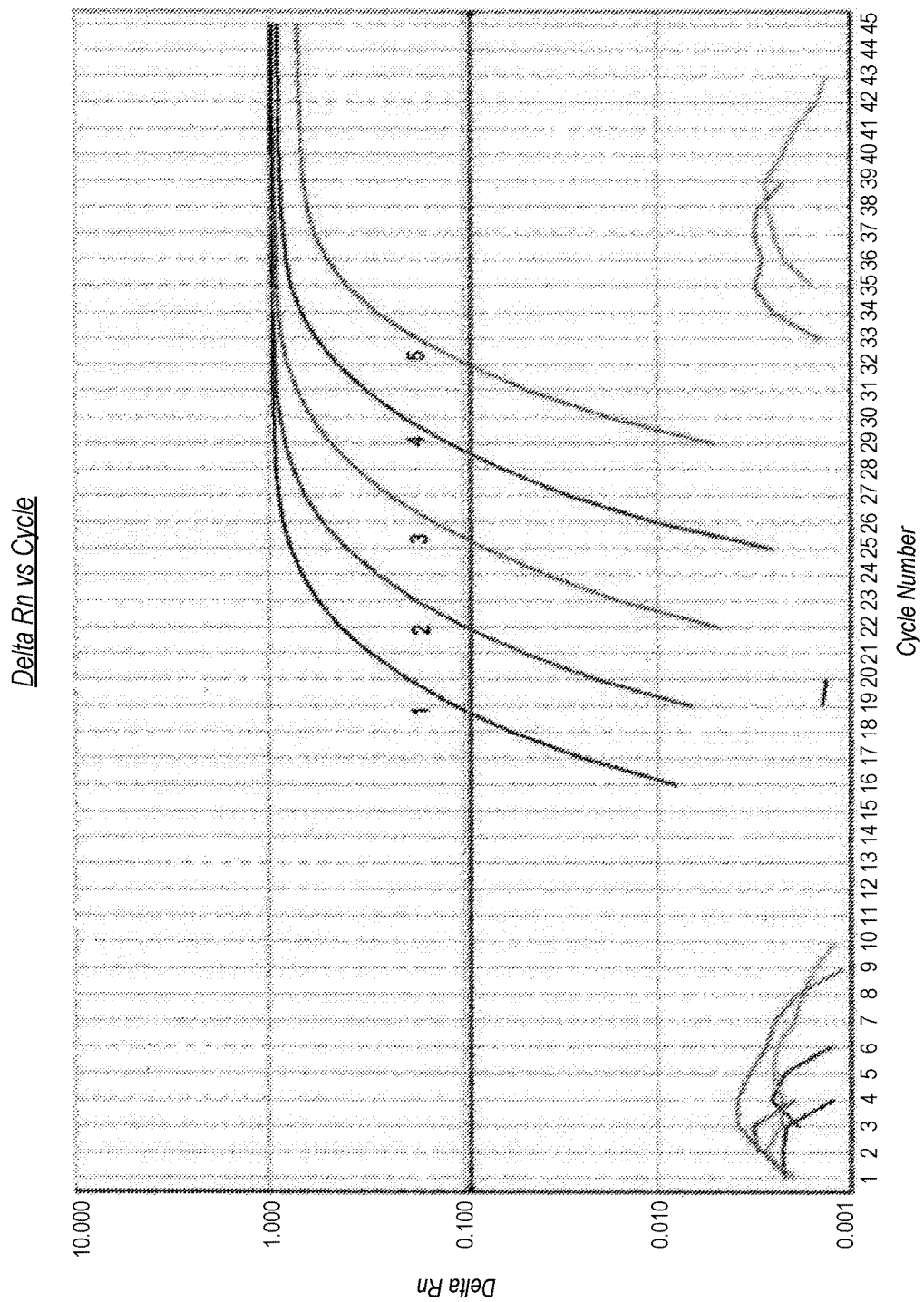
FIG. 3 shows WT1 mRNA amplification curves for various concentrations (in the graph, 1: $2.5 \times 10^5$ copies/test, 2: $2.5 \times 10^4$ copies/test, 3: $2.5 \times 10^3$ copies/test, 4: $2.5 \times 10^2$ copies/test, and 5: $2.5 \times 10^1$ copies/test) or the WT1 RNA standard when WT1 mRNA and GAPDH mRNA were amplified simultaneously (Example 1).
Figure 4:
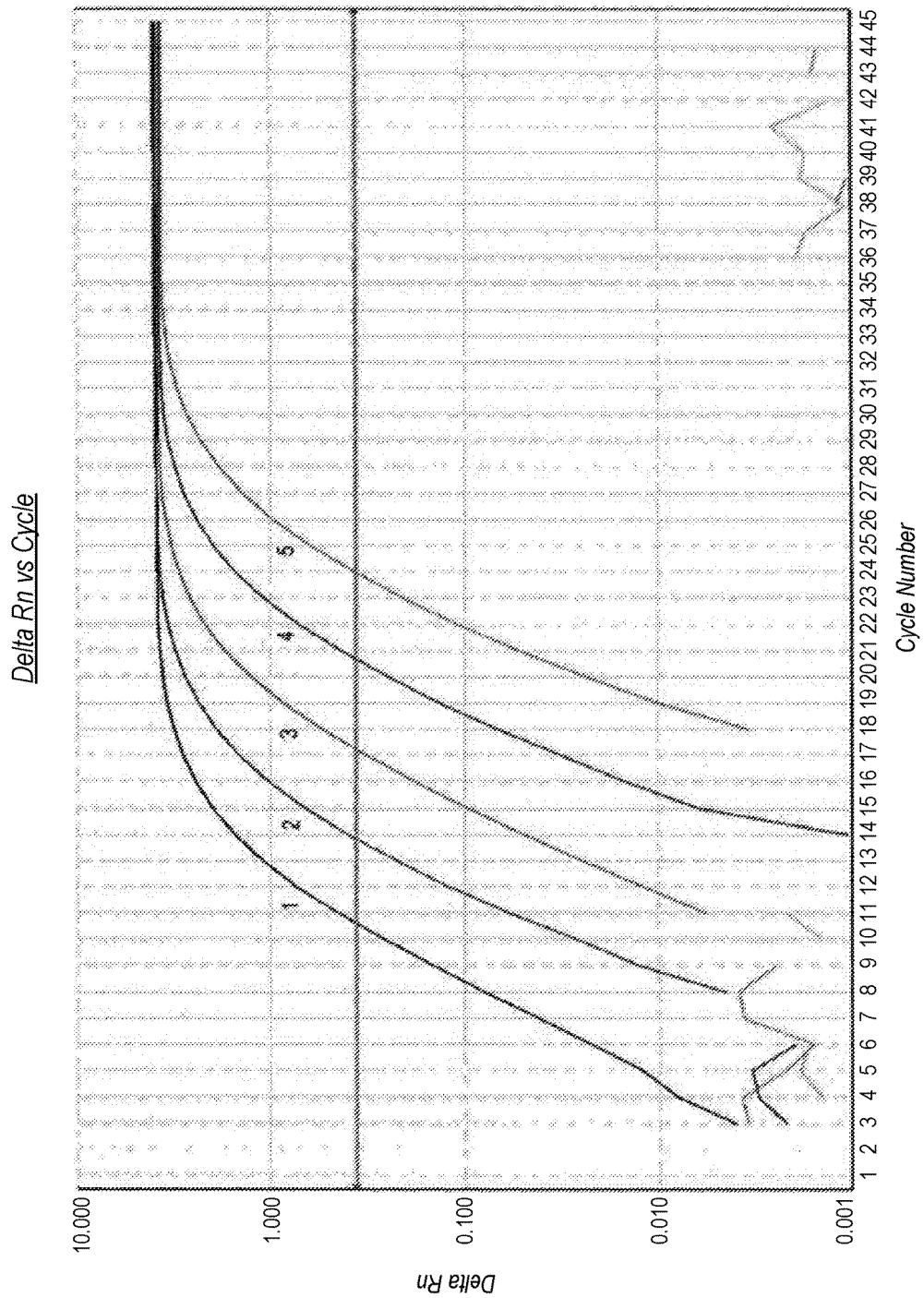
FIG. 4 shows GAPDH mRNA amplification curves for various concentrations (in the graph, 1: $1.0 \times 10^8$ copies/test, 2: $1.0 \times 10^7$ copies/test, 3: $1.0 \times 10^6$ copies/test, 4: $1.0 \times 10^5$ copies/test, and 5: $1.0 \times 10^4$ copies/test) of the GAPDH RNA standard when WT1 mRNA and GAPDH mRNA were amplified simultaneously (Example 1).

FIG. 1 shows (a) WT1 mRNA amplification curves for various concentrations of the WT1 RNA standard when WT1 mRNA was amplified alone, FIG. 2 shows (b) GAPDH mRNA amplification curves for various concentrations of the GAPDH RNA standard when GAPDH mRNA was amplified alone. FIG. 3 shows (c) WT1 mRNA amplification curves for various concentrations of the WT1 RNA standard when WT1 mRNA and GAPDH mRNA were amplified simultaneously, and FIG. 4 shows (d) GAPDH mRNA amplification curves for various concentrations of the GAPDH RNA standard when WT1 mRNA and GAPDH mRNA were amplified simultaneously. Table 4 shows the number of WT1 mRNA amplification cycles for various concentrations of the WT1 RNA standard when WT1 mRNA was amplified alone and when WT1 mRNA and GAPDH mRNA were amplified simultaneously. Table 5 shows the number of GAPDH mRNA amplification cycles for various concentrations of the GAPDH RNA standard when GAPDH mRNA was amplified alone and when WT1 mRNA and GAPDH mRNA were amplified simultaneously.

TABLE 4

Number of Amplification Cycles of WT1 mRNA

| Concentration of WT1 RNA Standard | WT1 mRNA Amplification Alone Number of Amplification Cycles | WT1 mRNA and GAPDH mRNA Simultaneous Amplification | |
|---|---|---|---|
| | | Number of Amplification Cycles | Difference in Number of Amplification Cycles from Amplification Alone |
| $2.5 \times 10^5$ copies/test | 18.63 | 18.67 | −0.04 |
| $2.5 \times 10^4$ copies/test | 21.87 | 21.90 | 0.03 |
| $2.5 \times 10^3$ copies/test | 25.18 | 25.24 | 0.06 |
| $2.5 \times 10^2$ copies/test | 28.59 | 28.53 | −0.06 |
| $2.5 \times 10^1$ copies/test | 32.09 | 31.94 | −0.15 |
| dH$_2$O (blank) | Not Detected | Not Detected | — |

TABLE 5

Number of Amplification Cycles of GAPDH mRNA

| Concentration of GAPDH RNA Standard | GAPDH mRNA Amplification Alone Number of Amplification Cycles | WT1 mRNA and GAPDH mRNA Simultaneous Amplification Number of Amplification Cycles | Difference in Number of Amplification Cycles from Amplification Alone |
|---|---|---|---|
| $1.0 \times 10^8$ copies/test | 10.18 | 10.30 | 0.12 |
| $1.0 \times 10^7$ copies/test | 13.66 | 13.83 | 0.17 |
| $1.0 \times 10^6$ copies/test | 17.06 | 17.16 | 0.10 |
| $1.0 \times 10^5$ copies/test | 20.35 | 20.55 | 0.20 |
| $1.0 \times 10^4$ copies/test | 23.68 | 23.85 | 0.17 |
| dH$_2$O (blank) | Not Detected | Not Detected | — |

FIG. 1 shows WT1 mRNA amplification curves when WT1 mRNA was amplified alone. As shown in FIG. 1, it was possible to detect WT1 mRNA at $2.5 \times 10^5$ to $2.5 \times 10^1$ copies/test when WT1 mRNA was amplified alone. As shown in FIG. 3, it was also possible to detect WT1 mRNA at $2.5 \times 10^5$ to $2.5 \times 10^1$ copies/test when. WT1 mRNA and GAPDH mRNA were amplified simultaneously.

In addition, as shown in Table 4, the difference between the number of amplification cycles when WT1 mRNA was amplified alone (number of amplification cycles: 18.63 to 32.09) and the number of amplification cycles when WT1 mRNA and GAPDH mRNA were amplified simultaneously (number of amplification cycles: 18.67 to 31.94) was as small as −0.15 to 0.06, and thus there was no significant difference in the number of amplification cycles between amplification alone and simultaneous amplification. From this result, it is thought that even when WT1 mRNA, which is a gene of interest, and the gene for correction are amplified simultaneously, WT1 mRNA can be detected at a comparable number of amplification cycles, as in the case in which the gene of interest (WT1 mRNA) is amplified alone.

FIG. 2 shows GAPDH mRNA amplification curves when GAPDH mRNA was amplified alone. As shown in FIG. 2, it was possible to detect GAPDH mRNA at $1.0 \times 10^8$ to $1.0 \times 10^4$ copies/test when GAPDH mRNA was amplified alone.

As shown in Table 5, the difference between the number of amplification cycles when GAPDH mRNA was amplified alone (10.18 to 23.68) and the number of amplification cycles when WT1 mRNA and GAPDH mRNA were amplified simultaneously (10.30 to 23.85) was 0.10 to 0.20; i.e., the difference in the number of amplification cycles between amplification alone and simultaneous amplification was not large. From this result, it is thought that even when GAPDH mRNA, which is a gene for correction, and WT1 mRNA, which is a gene of interest, are amplified simultaneously, GAPDH mRNA can be detected at a comparable number of amplification cycles, as in the case in which the gene for correction (GAPDH mRNA) is amplified alone.

Example 2

Dilution Test Using RNA Extracted from K562

In this Example, the measurement sensitivity was compared between one-step and multiplex RT-PCR in which WT1 mRNA and GAPDH mRNA were amplified simultaneously, and two-step RT-PCR in which a reverse transcription reaction, and PCR were individually performed in different vessels and WT1 mRNA and GAPDH mRNA were amplified separately. The two-step RT-PCR was performed using an Otsuka kit for measuring WT1 mRNA (Otsuka Pharmaceutical Co., Ltd.).

(1) Sequences of Primers and Probes

Table 6 shows the sequences of the primers and probes used for measuring WT1 mRNA and GAPDH mRNA by one-step RT-PCR. Since an Otsuka kit for measuring WT1 mRNA was used in two-step RT-PCR, the primers and probe in two-step RT-PCR were not known.

TABLE 6

Primer and Probe Sequences for Amplifying WT1 mRNA and GAPDH mRNA
(Sequence Set A)

| Gene | Primer | Sequence |
|---|---|---|
| WT1 | Forward Primer | SEQ ID NO: 3: CGCTATTCGCAATCAGGGTTAC |
|  | Reverse Primer | SEQ ID NO: 4: GGATCCTCATGCTTGAATGAGT |
|  | Probe | SEQ ID NO: 5: AGCACGGTCACCTTCGACGGGA |
| GAPDH | Forward Primer | SEQ ID NO: 6: CAGCCGAGCCACATCG |
|  | Reverse Primer | SEQ ID NO: 7: GTCAATGAAGGGGTCATTGATG |
|  | Probe | SEQ ID NO: 8: TTGGTCGTATTGGGCGCCTGG |

(2) Preparation of Standards

RNA standards prepared in the same manner as the method described in Example 1 were used, as standards (WT1 mRNA and GAPDH mRNA) in one-step RT-PCR. The concentration of the WT1 RNA standard was adjusted to $2.5 \times 10^1$, $2.5 \times 10^3$, $2.5 \times 10^5$, and $2.5 \times 10^7$ copies/test. The concentration of the GAPDH RNA standard was adjusted to $1.0 \times 10^3$, $1.0 \times 10^5$, $1.0 \times 10^7$, and $1.0 \times 10^9$ copies/test. The standards included in an Otsuka kit for measuring WT1 mRNA were used in two-step RT-PCR.

(3) Test Samples

RNA extracted from WT1-positive leukemia cell line K562 was used, as test samples. More specifically, total. RNA extracted from K562 was diluted with a TE buffer to final concentrations of 2, 5, and 10 μL to prevent non-specific nucleic acid adsorption to a tube, thereby obtaining test samples. The TE buffer contained E. coli transfer RNA as carrier RNA beforehand so that the final concentration was 50 ng/μL.

(4) RT-PCR Reaction

One-step RT-PCR was performed in the same manner as in Example 1. Two-step RT-PCR was performed using an Otsuka kit for measuring WT1 mRNA (Otsuka Pharmaceutical Co., Ltd.) according to its package insert. The measurement was performed in duplicate for each test sample. The measurement results were calculated as copy/µgRNA, which is the number of WT1 mRNA per µg of total RNA, according to the package insert of the Otsuka kit for measuring WT1 mRNA.

(5) Results (5-1) Results of Dilution Measurement Using RNA Extracted from K562

Table 7 shows the results of a dilution test performed using RNA extracted from K562 as test samples by one-step RT-PCR and two-step RT-PCR.

TABLE 7

K562 RNA Measurement Results

| RNA Concentration | One-step RT-PCR (copy/µgRNA) | | | Two-step RT-PCR (copy/µgRNA) | | |
|---|---|---|---|---|---|---|
| | First | Second | Average | First | Second | Average |
| 10 pg/µL | 17.4 | 19.6 | 18.5 | 21.6 | 23.0 | 22.3 |
| 5 pg/µL | 14.2 | 11.2 | 12.7 | 17.2 | 1.9 | 9.5 |
| 2.5 pg/µL | 3.3 | 7.6 | 5.5 | Not Detected | Not Detected | — |

As shown in Table 7, in the one-step RT-PCR, it was possible to measure RNA extracted from R562 even when it was diluted up to an RNA concentration of 2.5 pg/µL. In contrast, in two-step RT-PCR, no amplification signal by PCR was detected when RNA extracted from K562 was diluted up to an RNA concentration of 2.5 pg/µL, and the duplicate measurement data for 5 pg/µL showed a discrepancy, i.e., 17.2 and 1.9 copy/µgRNA. Thus, the range measurable as an effective value was considered to be up to 10 pg/µL. These results reveal that the measurement sensitivity is better in one-step RT-PCR than in two-step RT-PCR.

Example 3

Cross-Reactivity Test

In this Example, one-step RT-PCR in which WT1 mRNA and GAPDH mRNA were amplified simultaneously was performed using the set shown in Table 8 (sequence set B) as primers and probes and also separately using the set shown in Table 9 as primers and probes, and cross reactivity was evaluated.

TABLE 8

Primer and Probe Sequences for Amplifying WT1 mRNA and GAPDH mRNA
(Sequence Set B)

| Gene | Primer/Probe | Sequence | Gene Region |
|---|---|---|---|
| WT1 | Forward Primer | SEQ ID NO: 9: GATAACCACACAACGCCCATC | 1214-1234* |
| | Reverse Primer | SEQ ID NO: 10: CACACGTCGCACATCCTGAAT | 1303-1283* |
| | Probe | SEQ ID NO: 11: AATACACACGCACGGTGTCTTCAGAG | 1255-1280* |
| GAPDH | Forward Primer | SEQ ID NO: 6: CAGCCGAGCCACATCG | 77-92** |
| | Reverse Primer | SEQ ID NO: 12: TGATGGCAACAATATCCACTTTACC | 202-178** |
| | Probe | SEQ ID NO: 8: TTGGTCGTATTGGGCGCCTGG | 134-154** |

A single asterisk indicates a region of the human WT1 gene (NM_024426.4: SEQ ID NO: 1).
Double astisks indicates a region of the humna GAPDH gene (NM_002046.3: SEQ ID NO: 2).

TABLE 9

Primer and Probe Sequences for Amplifying WT1 mRNA and GAPDH mRNA
(Comparative Set)

| Gene | Primer/Probe | Sequence | Gene Region |
|---|---|---|---|
| WT1 | Forward Primer | SEQ ID NO: 9: GATAACCACACAACGCCCATC | 1214-1234* |
| | Reverse Primer | SEQ ID NO: 10: CACACGTCGCACATCCTGAAT | 1303-1283* |
| | Probe | SEQ ID NO: 11: AATACACACGCACGGTGTCTTCAGAG | 1255-1280* |
| GAPDH | Forward Primer | SEQ ID NO: 13: CCGCATCTTCTTTTGCGTC | 56-74** |
| | Reverse Primer | SEQ ID NO: 12: TGATGGCAACAATATCCACTTTACC | 202-178** |
| | Probe | SEQ ID NO: 8: TTGGTCGTATTGGGCGCCTGG | 134-154** |

A single asterisk indicates a region of the human WT1 gene (NM_024426.4: SEQ ID NO: 1).
Double astisks indicates a region of the humna GAPDH gene (NM_002046.3: SEQ ID NO: 2).

As test samples, 250 ng, 50 ng, and 10 ng of human genome DNA (Merck KGaA, Darmstadt, Germany, Cat. No. 69237) and 250 ng of total RNA extracted from WT1-positive leukemia cell line K562 (WT1 K562) were used.

One-step RT-PCR was performed in the same manner as in Example 1. Further, amplification products obtained by subjecting human genome DNA and WT1 K562 mRNA to PCR were subjected to agarose gel electrophoresis under the following conditions to confirm the amplification products. The agarose gel electrophoresis was performed according to an ordinary method.

Figure 5:
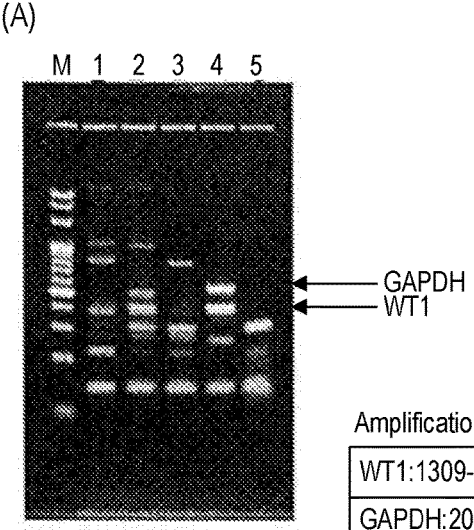
FIG. 5 shows the results obtained by performing one-step RT-PCR in which WT1 mRNA and GAPDH mRNA are amplified simultaneously, using (A) the set shown in Table 8 (sequence set B) as primers and probes and also separately using (B) the set shown in Table 9 (comparative set) as primers and probes, and subjecting the thus-obtained amplification products to agarose gel electrophoresis.
Figure 5:
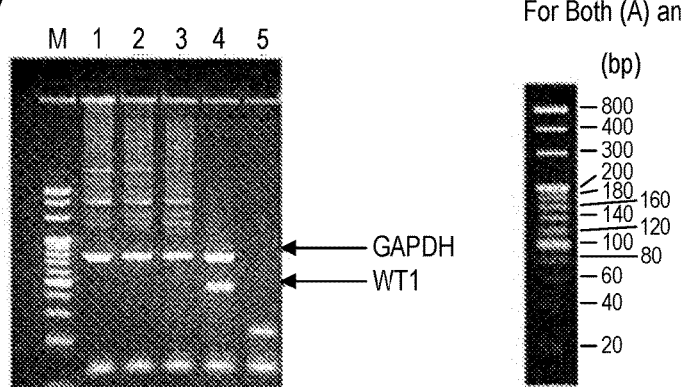

Agarose Gel Electrophoresis Conditions
Electrophoresis Conditions: 15 min, 4% E-gal,
Photo Conditions: Filter for SYBR,
  Directly photographed with an E-gal apparatus
  Shutter Speed: 1/15
  Aperture: 4.5
Application Conditions: Sample 2.5 µL+dH$_2$O 16.5 µL
Marker 2.5 µL+dH$_2$O 16.5 µL
Results It is known that GAPDH gene is not present in human genomic DNA, but GAPDH pseudogenes are. In this Example, when one-step RT-PCR was performed using the sequences of the primers and probes shown in Table 8, no band corresponding to GAPDH was observed in human genome DMA by electrophoresis, as shown in lanes 1 to 3 of FIG. 5(A). More specifically, it was confirmed that the one-step RT-PCR using the primers and probes of the present invention enables GAPDH to be clearly distinguished from GAPDH pseudogenes and does not misidentify GAPDH pseudogenes as GAPDH. In contrast, when one-step RT-PCR using the sequences of the primers and probes shown in Table 9 was performed, bands corresponding to GAPDH were observed by electrophoresis, as shown in lanes 1 to 3 of FIG. 5(B). That is, it was not possible to distinguish GAPDH from GAPDH pseudogenes in the one-step RT-PCR using these primers and probes.

For reference, Tables 10 and 11 respectively show the number of amplification cycles for GAPDH and WT1 when one-step RT-PCR was performed using the sequences of the primers and probes shown in Table 8 (Example) and when one-step RT-PCR was performed using the sequences of the primers and probes shown in Table 9 (Comparative Example). In the tables, "ND" means not detectable.

TABLE 10

Number of Amplification Cycles for GAPDH

| Sample | Example Number of Amplification Cycles (Sequence Set B) | Comparative Example Number of Amplification Cycles (Comparative Set) |
|---|---|---|
| Human Genomic DNA 250 ng/test | ND | 19.28 |
| Human Genomic DNA 50 ng/test | ND | 21.41 |
| Human Genomic DNA 10 ng/test | ND | 23.83 |
| K562 250 ng/test | 13.80 | 13.09 |

ND: Not Detected

TABLE 11

Number of Amplification Cycles for WT1

| Sample | Example Number of Amplification Cycles (Sequence Set B) | Comparative Example Number of Amplification Cycles (Comparative Set) |
|---|---|---|
| Human Genomic DNA 250 ng/test | ND | ND |
| Human Genomic DNA 50 ng/test | ND | ND |
| Human Genomic DNA 10 ng/test | ND | ND |
| K562 250 ng/test | 21.69 | 22.59 |

Sequence Listing Free Text

The base sequences set forth in SEQ ID NOs: 3 to 12 mean the primers and probes shown in Table 3. The correspondence is as detailed in Table 3. The base sequence set forth in SEQ ID NO: 13 means the base sequence of the primer shown in Table 9. This base sequence corresponds to the base sequence of the 56-74 region of the human GAPDH gene (NM_002046.3: SEQ ID NO: 2).

The invention claimed is:

1. A method for quantifying the expression level of human WT1 mRNA in a test sample by one-step reverse transcription PCR, the method comprising simultaneously subjecting the human WT1 mRNA and a housekeeping gene to reverse transcription and extension reactions carried out sequentially in the test sample in the same vessel, wherein the housekeeping gene is GAPDH mRNA;

wherein the following (a) and (c-1) are used for PCR amplification of the human WT1 mRNA and the housekeeping gene, respectively, or the following (b) and (c-2) are used for PCR amplification of the human WT1 mRNA and the housekeeping gene, respectively:

(a) a primer set comprising a forward PCR primer consisting of the base sequence set forth in SEQ ID NO: 3 and a reverse PCR primer consisting of the base sequence set forth in SEQ ID NO: 4, and (c-1) a primer set comprising a forward PCR primer consisting of the base sequence set forth in SEQ ID NO: 6 and a reverse PCR primer consisting of the base sequence set forth in SEQ ID NO: 7, or (b) a primer set comprising a forward PCR primer consisting of the base sequence set forth in SEQ ID NO: 9 and a reverse PCR primer consisting of the base sequence set forth in SEQ ID NO: 10, and (c-2) a primer set comprising a forward PCR primer consisting of the base sequence set forth in SEQ ID NO: 6 and a reverse PCR primer consisting of the base sequence set forth in SEQ ID NO: 12.

2. The method according to claim 1, wherein the following (a') and (c'-1) are used for PCR amplification of the human WT1 mRNA and the housekeeping gene, respectively, or the following (b') and (c'-2) are used for PCR amplification of the human WT1 mRNA and the housekeeping gene, respectively:

(a') a primer set comprising a forward PCR primer consisting of the base sequence set forth in SEQ ID NO: 3 and a reverse PCR primer consisting of the base sequence set forth in SEQ ID NO: 4, and a probe consisting of the base sequence set forth in SEQ ID NO: 5, the probe being labeled, and (c'-1) a primer set comprising a forward PCR primer consisting of the base sequence set forth in SEQ ID NO: 6 and a reverse PCR primer consisting of the base sequence set forth in SEQ ID NO: 7, and a probe consisting of the base sequence set forth in SEQ ID NO: 8, the probe being labeled, or (b') a primer set comprising a forward PCR primer consisting of the base sequence set forth in SEQ ID NO: 9 and a reverse PCR primer consisting of the base sequence set forth in SEQ ID NO: 10, and a probe consisting of the base sequence set forth in SEQ ID NO: 11, the probe being labeled, and (c'-2) a primer set comprising a forward PCR primer consisting of the base sequence set forth in SEQ ID NO: 6 and a reverse PCR primer consisting of the base sequence set forth in SEQ ID NO: 12, and a probe consisting of the base sequence set forth in SEQ ID NO: 8, the probe being labeled.

3. A kit for reverse transcription real-time PCR for quantifying the expression level of human WT1 mRNA, the kit comprising the following (a), (c-1) and (d), or (b), (c-2) and (d):

(a) a primer set comprising a forward PCR primer consisting of the base sequence set forth in SEQ ID NO: 3 and a reverse PCR primer consisting of the base sequence set forth in SEQ ID NO: 4, and a sequence-specific binding probe used for detecting amplification product amplified by the primer set, the probe being labeled, (c-1) a primer set comprising a forward PCR primer consisting of the base sequence set forth in SEQ ID NO: 6 and a reverse PCR primer consisting of the base sequence set forth in SEQ ID NO: 7, and a sequence-specific binding probe used for detecting amplification product amplified by the primer set, the probe being labeled, and (d) at least one component selected from the group consisting of dNTPs, Mg salts, buffering components for pH adjustment, enzymes having reverse transcription activity, components for stabilizing an enzyme, ribonuclease inhibitors, and a reaction vessel, or (b) a primer set comprising a forward PCR primer consisting of the base sequence set forth in SEQ ID NO: 9 and a reverse PCR primer consisting of the base sequence set forth in SEQ ID NO: 10, and a sequence-specific binding probe used for detecting amplification product amplified by the primer set, the probe being labeled, and (c-2) a primer set comprising a forward PCR primer consisting of the base sequence set forth in SEQ ID NO: 6 and a reverse PCR primer consisting of the base sequence set forth in SEQ ID NO: 12, and a sequence-specific binding probe used for detecting amplification product amplified by the primer set, the probe being labeled, and and the above-mentioned (d).

4. A kit for reverse transcription real-time PCR for quantifying the expression level of human WT1 mRNA, the kit comprising the following (a'), (c'-1) and (d), or (b'), (c'-2) and (d):

(a') a primer set comprising a forward PCR primer consisting of the base sequence set forth in SEQ ID NO: 3 and a reverse PCR primer consisting of the base sequence set forth in SEQ ID NO: 4, and a probe consisting of the base sequence set forth in SEQ ID NO: 5, the probe being labeled, (c'-1) a primer set comprising a forward PCR primer consisting of the base sequence set forth in SEQ ID NO: 6 and a reverse PCR primer consisting of the base sequence set forth in SEQ ID NO: 7, and a probe consisting of the base sequence set forth in SEQ ID NO: 8, the probe being labeled, and (d) at least one component selected from the group consisting of dNTPs, Mg salts, buffering components for pH adjustment, enzymes having reverse transcription activity, components for stabilizing an enzyme, ribonuclease inhibitors, and a reaction vessel, or (b') a primer set comprising a forward PCR primer consisting of the base sequence set forth in SEQ ID NO: 9 and a reverse PCR primer consisting of the base sequence set forth in SEQ ID NO: 10, and a probe consisting of the base sequence set forth in SEQ ID NO: 11, the probe being labeled, (c'-2) a primer set comprising a forward PCR primer consisting of the base sequence set forth in SEQ ID NO: 6 and a reverse PCR primer consisting of the base sequence set forth in SEQ ID NO: 12, and a probe consisting of the base sequence set forth in SEQ ID NO: 8, the probe being labeled, and the above-mentioned (d).

\* \* \* \* \*